United States Patent
Frey et al.

(10) Patent No.: US 10,876,054 B2
(45) Date of Patent: *Dec. 29, 2020

(54) OLEFIN AND BTX PRODUCTION USING ALIPHATIC CRACKING REACTOR

(71) Applicant: UOP LLC, Des Plaines, IL (US)

(72) Inventors: Stanley J. Frey, Palatine, IL (US); Hayim Abrevaya, Kenilworth, IL (US); Gregory R. Werba, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,400

(22) Filed: Jun. 1, 2018

(65) Prior Publication Data
US 2018/0273859 A1  Sep. 27, 2018

Related U.S. Application Data

(63) Continuation of application No. PCT/US2016/063126, filed on Nov. 21, 2016.
(Continued)

(51) Int. Cl.
  *C10G 63/04*   (2006.01)
  *C07C 4/18*    (2006.01)
  (Continued)

(52) U.S. Cl.
  CPC .............. *C10G 63/04* (2013.01); *C07C 4/18* (2013.01); *C10G 35/065* (2013.01); *C10G 35/22* (2013.01);
  (Continued)

(58) Field of Classification Search
  None
  See application file for complete search history.

(56) References Cited

U.S. PATENT DOCUMENTS 3,060,116 A    10/1962   Hardin, Jr. et al.
3,827,969 A    8/1974    Wilson et al.
(Continued)

FOREIGN PATENT DOCUMENTS

CN    1451036 A       10/2003
CN    103261124 A     8/2013
(Continued)

OTHER PUBLICATIONS

Search report from corresponding Russian patent application No. 2018127189/04(043300), dated Apr. 17, 2019.
(Continued)

*Primary Examiner* — In Suk C Bullock
*Assistant Examiner* — Alyssa L Cepluch (57) ABSTRACT

A process and apparatus for making aromatics are described. The process includes reforming a naphtha stream in a reforming zone to form a reformer effluent comprising aromatic compounds and non-aromatic compounds, wherein at least a portion of the aromatic compounds contain alkyl groups. The reformer effluent is heated and passed directly to an acid cracking reaction zone. The non-aromatic compounds are selectively cracked and at least a portion of the alkyl groups on the aromatic compounds are selectively dealkylated in the presence of an acid cracking catalyst to form a cracked reformer effluent comprising the aromatic compounds and cracked olefins.

15 Claims, 4 Drawing Sheets

Related U.S. Application Data (60) Provisional application No. 62/273,073, filed on Dec. 30, 2015.

(51) Int. Cl.
*C10G 47/16* (2006.01)
*C10G 61/10* (2006.01)
*C10G 35/06* (2006.01)
*C10G 35/22* (2006.01)
*B01J 29/40* (2006.01)

(52) U.S. Cl.
CPC ............ *C10G 47/16* (2013.01); *C10G 61/10* (2013.01); *B01J 29/40* (2013.01); *C07C 2529/40* (2013.01); *C10G 2300/104* (2013.01); *C10G 2300/1037* (2013.01); *C10G 2300/1044* (2013.01); *C10G 2300/807* (2013.01); *C10G 2400/20* (2013.01); *C10G 2400/30* (2013.01)

(56) References Cited

U.S. PATENT DOCUMENTS

| | | | |
|---|---|---|---|
| 3,928,174 | A | 12/1975 | Bonacci et al. |
| 4,158,026 | A | 6/1979 | Addison |
| 4,199,556 | A | 4/1980 | Plank et al. |
| 4,827,069 | A | 5/1989 | Kushnerick et al. |
| 4,992,607 | A | 2/1991 | Harandi et al. |
| 5,082,983 | A | 1/1992 | Breckenridge et al. |
| 5,865,986 | A * | 2/1999 | Buchanan ............ C10G 59/02 208/134 |
| 6,124,227 | A * | 9/2000 | Yao ........................ B01J 29/061 502/63 |
| 6,398,947 | B2 * | 6/2002 | Beck ....................... C10G 59/00 208/134 |
| 7,314,963 | B2 * | 1/2008 | Voskoboynikov ..... B01J 29/035 585/651 |
| 7,317,133 | B2 | 1/2008 | Vora et al. |
| 7,803,330 | B2 | 9/2010 | Vora et al. |
| 8,940,950 | B2 | 1/2015 | Ellrich et al. |
| 2010/0331590 | A1 | 12/2010 | Majumder et al. |
| 2013/0296623 | A1 | 11/2013 | Iaccino et al. |
| 2014/0100402 | A1 | 4/2014 | Gawlik et al. |
| 2014/0350315 | A1 * | 11/2014 | Ghosh ................... B01J 35/002 585/321 |
| 2015/0284646 | A1 * | 10/2015 | Fanget .................. C10G 63/04 585/321 |

FOREIGN PATENT DOCUMENTS

| | | |
|---|---|---|
| GB | 930512 | 7/1961 |
| GB | 2162534 | 2/1986 |
| RU | 2013146967 A | 4/2015 |
| WO | 9713826 A1 | 4/1997 |
| WO | 99057230 A1 | 11/1999 |
| WO | 2012015540 A2 | 2/2012 |
| WO | 2015128317 A1 | 9/2015 |

OTHER PUBLICATIONS

Written Opinion of the International Searching Authority from corresponding PCT application No. PCT/US2016/063126, dated Feb. 9, 2017.
International Preliminary Report on Patentability from corresponding PCT application No. PCT/US2016/063126, dated Jul. 3, 2018.
International Search Report from corresponding PCT application No. PCT/US2016/063126, dated Feb. 27, 2017.
International Search Report from PCT application No. PCT/US2017/056937, dated Feb. 14, 2018.
Written Opinion from PCT application No. PCT/US2017/056937, dated Feb. 1, 2018.
International Preliminary Report on Patentability from PCT application No. PCT/US2017/56937, dated Jul. 2, 2019.
Mei Li, et al., "General Chemistry", pp. 275-276, Shanghai Jiaotong University Press, Jul. 2015.
Zi Gao, et al.,"Technology for Zeolite Catalysis and Separation", pp. 41, 44, 47 and 51-52, China Petrochemical Press, Nov. 1999.
Xianlin Hou, et al., "China's Oil Refining Technology (Second Edition)", pp. 475-478, China Petrochemical Press, Jul. 2001.

* cited by examiner

OLEFIN AND BTX PRODUCTION USING ALIPHATIC CRACKING REACTOR

CROSS-REFERENCE TO RELATED APPLICATIONS

This application is a Continuation of copending International Application No. PCT/US2016/063126 filed Nov. 21, 2016, which application claims priority from U.S. Provisional Application No. 62/273,073 filed Dec. 30, 2015, the contents of which cited applications are hereby incorporated by reference in their entirety.

BACKGROUND

Aromatics, particularly benzene, toluene, ethylbenzene, and the xylenes (ortho, meta, and para isomers), which are commonly referred to as "BTEX" or more simply "BTX," are extremely useful chemicals in the petrochemical industry. They represent the building blocks for materials such as polystyrene, styrene-butadiene rubber, polyethylene terephthalate, polyester, phthalic anhydride, solvents, polyurethane, benzoic acid, and numerous other components. Conventionally, BTX is obtained for the petrochemical industry by separation and processing of fossil-fuel petroleum fractions, for example, in catalytic reforming or cracking refinery process units, followed by BTX recovery units.

Typically, integrated refining-petrochemical complexes separate a crude feedstock into a "straight run" or desired fraction of naphtha, such as $C_6$-$C_{10}$ naphtha, i.e., naphtha containing hydrocarbons having carbon chain lengths of six to ten, and a heavier fraction containing longer chain hydrocarbons such as heavy oils and residues. The naphtha stream typically undergoes reforming to produce a reformate with an increased aromatic content. The reformate is processed in an aromatics complex to produce selected aromatic products, such as benzene and para-xylene.

Some of the naphtha, typically about 5-20% of the $C_{5+}$ reformer feed stream remains as aliphatic $C_{5+}$ hydrocarbon in the reformate after the reforming reaction. The reformate is separated from the $C_{4-}$ components in a flash separator and a debutanizer column, and then split in a distillation column between the $A_{7-}$ and $A_{8+}$ fractions. The aliphatics are in the $A_{7-}$ fraction and are separated in an extractive distillation unit, which commonly uses Sulfolane solvent) as a raffinate from the benzene and toluene. The benzene is further fractionated as a pure petrochemical product. The raffinate is then normally blended into gasoline or sent to a thermal cracking unit to produce ethylene, propylene, and heavier components.

Figure 1:
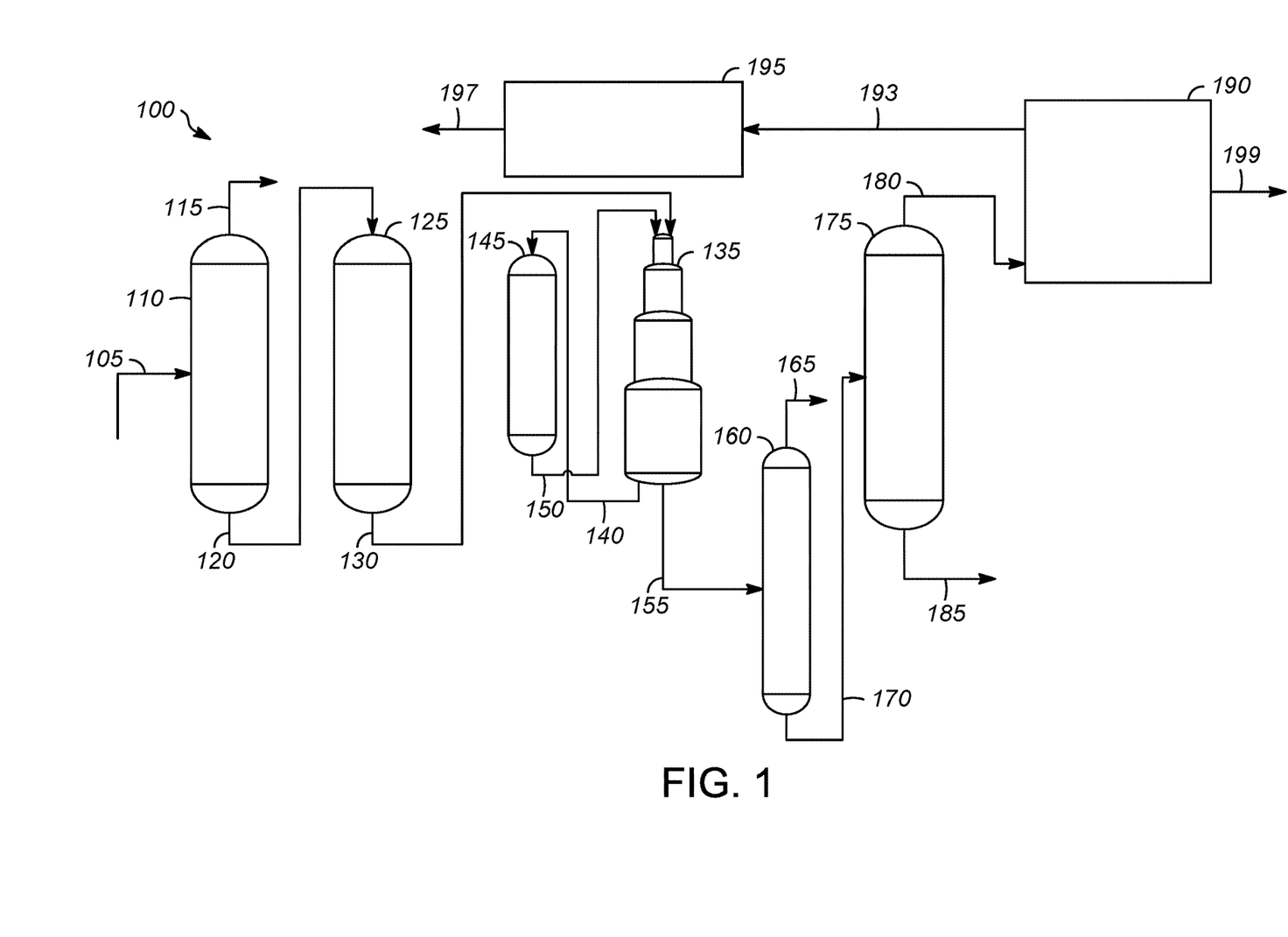
FIG. 1 is an illustration of a process for converting naphtha into aromatics.

FIG. 1 shows one embodiment of a process 100 for converting naphtha into aromatics. The naphtha feed 105 is sent to a naphtha splitter 110 where it is separated into an overhead stream 115 having a T5 boiling point in a range of about 0° C. to about 34° C. and a T95 boiling point in a range of about 20° C. to about 82° C. and a bottoms stream 120 having a T5 boiling point in a range of about 20° C. to about 82° C. and a T95 boiling point in a range of about 140° C. to about 215° C. The bottoms stream 120 is sent to a naphtha hydrotreating unit 125 to form a hydrotreated stream 130. The hydrotreated stream 130 is sent to a reformer 135. A catalyst stream 140 from the bottom of the reformer 135 is sent to a catalyst regenerator 145. The regenerated catalyst 150 is sent to the top of the reformer 135. The reformer effluent 155 is sent to a debutanizer column 160 where a $C_{4-}$ stream 165 is removed. The stripper bottoms stream 170 is sent to a reformate splitter column 175 into an $A_{7-}$ stream 180, which contains $A_{7-}$ and the aliphatic compounds, and an $A_{8+}$ stream 185. The $A_{7-}$ stream 180 is sent to the extractive distillation zone 190 where the $A_{7-}$ aromatics are separated from the raffinate containing the aliphatic compounds. The aromatics lean raffinate stream 193 is sent to a thermal cracking zone 195 to produce stream 197 comprising ethylene, propylene, and heavier components. The aromatics rich $A_{7-}$ stream 199 is sent for further processing in the aromatics complex.

However, the reformate splitter column and the extractive distillation unit, which includes 3 distillation columns, are expensive to build and to operate. In addition, the utilization of the raffinate stream 193 or light boiling naphtha streams with T95 boiling point of less than 82° C. is often difficult as it has relatively low octane and high vapor pressure for gasoline blending or it requires a large investment in a naphtha steam thermal cracking unit to convert to ethylene and propylene.

Therefore, there is a need for processes for converting naphtha into aromatics which reduce or eliminate the need for expensive distillation columns and improve the value of the raffinate stream and other light naphthas at lower capital cost.

SUMMARY OF THE INVENTION

One aspect of the invention is a process for making aromatics. In one embodiment, the process includes reforming a naphtha stream in a reforming zone under reforming conditions to form a reformer effluent comprising aromatic compounds and non-aromatic compounds, wherein at least a portion of the aromatic compounds contain alkyl groups. The reformer effluent is heated and passed directly to an acid cracking reaction zone. The non-aromatic compounds are selectively cracked and at least a portion of the alkyl groups on the aromatic compounds are selectively dealkylated in the presence of an acid cracking catalyst in the acid cracking reaction zone under acid cracking conditions to form a cracked reformer effluent comprising the aromatic compounds and cracked olefins.

Another aspect of the invention is an apparatus. In one embodiment, the apparatus includes a reforming zone having an inlet and an outlet; an acid cracking reaction zone having an inlet and an outlet, the inlet of the acid cracking zone being in fluid communication with the outlet of the reforming zone; a fractionation column having an inlet, an overhead outlet, and a bottoms outlet, the inlet of the fractionation zone being in fluid communication with the outlet of the acid cracking reaction zone; and an aromatics recovery zone having an inlet and an outlet, the inlet of the aromatic complex being in fluid communication with the bottoms outlet of the fractionation zone.

DETAILED DESCRIPTION OF THE INVENTION

The present invention involves acid cracking the reformer effluent directly without separating the reformer effluent into its various components. The aliphatics remaining in the reformate are converted directly to at least one of ethylene, propylene, and butylene at conversion rates of 80% or more. Furthermore, there is a concurrent increase in aromatic rings, hydrogen, and significant dealkylation of the ethyl and longer substituents on the aromatic rings.

The process produces at least one of ethylene, propylene, and butylene directly from the reformer, reducing or eliminating the need to send the aliphatics to an aromatic extractive distillation section and thermal naphtha cracker. The process also converts a large amount of the benzene co-boiler material, which may reduce the intensity of, or eliminate the need for, an aromatics extraction section for benzene purification. In addition, the increase in the production of aromatics will lead to higher production of combined benzene and para-xylene from the aromatics complex for a given amount of naphtha feed. Furthermore, the dealkylation of ethyl and longer aromatic substituents on the aromatic compounds from the reformer will add to the yield of light olefins and decrease the size of equipment and utilities in the aromatics complex by reducing the amount of ethylbenzene circulating in the para-xylene (PX) extraction xylene isomerization loop and reducing the amount of dealkylation required in the transalkylation reactor.

A naphtha feed stream is reformed to form aromatics, such as BTX and non-aromatic compounds, such as $C_5$, $C_6$ and $C_7$ branched and normal paraffins and cyclic paraffins. The reforming zone effluent is heated and passed directly to an acid cracking reaction zone. By passing directly to an acid cracking reaction zone, we mean that the reformer effluent stream's composition is not changed by separation into component streams (e.g., the reformer effluent stream is not fractionated). However, the composition can be changed by adding one or more streams to the reforming zone effluent stream. Examples of suitable acid cracking reaction zones include, but are not limited to, fixed bed reactors, fluidized bed reactors, and ebullated bed reactors. The acid catalyst could be continuously regenerated, for example in a continuous catalyst regenerator or a swing bed reactor.

The acid cracking catalyst has an MFI type framework and does not include a hydrogenating metal function. Suitable acid cracking catalysts include, but are not limited to ZSM-5 catalysts. For example a silicalite catalyst can be used. In some embodiments, the silicalite catalyst can have a zeolite silica to alumina molar ratio of greater than about 250, or greater than about 300, or greater than about 400, or greater than about 500.

The non-aromatic compounds in the reformer effluent are selectively cracked to form cracked olefins, including at least one of ethylene, propylene, and butylene. The effluent from the acid cracking reaction zone contains aromatics from the reforming zone effluent and the cracked olefins from the cracking reaction zone, as well as additional produced aromatics, cracked paraffins, and hydrogen.

The effluent from the acid cracking reaction zone is separated into an aromatic rich stream and an aromatic lean stream. By aromatic rich stream, we mean a stream containing at least about 90% aromatic compounds, or at least about 95%, or at least about 97%, or at least about 99%. By aromatic lean stream, we mean a stream containing less than about 30% aromatic compounds, or less than about 20%, or less than about 10%.

The aromatic rich stream can be recovered and used to produce benzene and/or para-xylene. In some embodiments, the aromatic rich stream can be passed directly to an aromatics complex without subjecting a substantial amount of the aromatic rich stream to a distillation zone or a liquid-liquid extraction process for aromatics in an integrated process. In some embodiments, at least 50 wt % of the recovered aromatics stream is sent to the aromatics complex without being subjected to distillation or extraction, or at least about 60 wt %, or at least about 70 wt %, or at least about 75 wt %, or at least about 80 wt %, or at least about 85 wt %, or at least about 90 wt %, or at least about 95 wt %.

Typically, at least some of the aromatic compounds contain alkyl groups. In some embodiments, at least a portion of the ethyl and larger alkyl groups on the aromatic compounds are dealkylated in the selective cracking zone to form additional olefins, comprising at least one of ethylene, propylene, and butylene.

The temperature in the acid cracking reaction zone may be in the range of about 475° C. to about 650° C., or about 500° C. to about 625° C. The pressure can be in the range of in a range of about 30 kPa (g) to about 750 kPa (g), or about 100 kPa (g) to about 400 kPa (g). The ratio of hydrogen to hydrocarbon ratio is at least about 0.5:1, or at least about 2:1, or at least about 4:1.

In some embodiments, the feed stream to the reforming zone can be formed by introducing a naphtha stream to a naphtha splitter column. The naphtha stream is split into at least two streams. In some embodiments, the naphtha stream is split into an overhead stream having a T5 boiling point in a range of about 0° C. to about 34° C. and a T95 boiling point in a range of about 20° C. to about 82° C., and a bottoms stream having a T5 boiling point in a range of about 20° C. to about 82° C. and a T95 boiling point in a range of about 140° C. to about 215° C. The bottoms stream is sent to a naphtha hydrotreating reaction zone to form a hydrotreated naphtha stream. The hydrotreated naphtha stream could then be introduced into the reforming zone. In some embodiments, the overhead stream from the naphtha splitter column can be sent to the acid cracking reaction zone, and the hydrocarbons in the overhead stream can be selectively cracked to form additional olefins. However, if this is done, the naphtha hydrotreating should precede the naphtha splitter to remove sulfur and nitrogen compounds.

In some embodiments, an additional stream (not shown) having a T5 boiling point in a range of about 0° C. to about 34° C. and a T95 boiling point in a range of about 20° C. to about 82° C. can be sent to the acid cracking reaction zone. Suitable sources for the additional stream can be light naphtha from hydrotreated straight run naphtha, light naphtha from straight run naphtha, aromatics extraction raffinate, hydrocracked light naphtha, gas oil fluidized catalytic cracker light naphtha, or combinations thereof.

In some embodiments, the cracked olefins, comprising at least one of ethylene, propylene, and butylene, from the acid cracking reaction zone are recovered. In some embodiments, the aromatic lean fraction is sent to a steam cracking zone to form additional olefins, comprising at least one of ethylene, propylene, and/or butylene, which are then recovered along with the cracked olefins formed in the acid cracking reaction zone. The recovered cracked olefins and additional olefins can be greater than about 90 wt % pure, or greater than about 95 wt %, or greater than about 99 wt-%, or greater than about 99.5 wt-%.

Figure 2A:
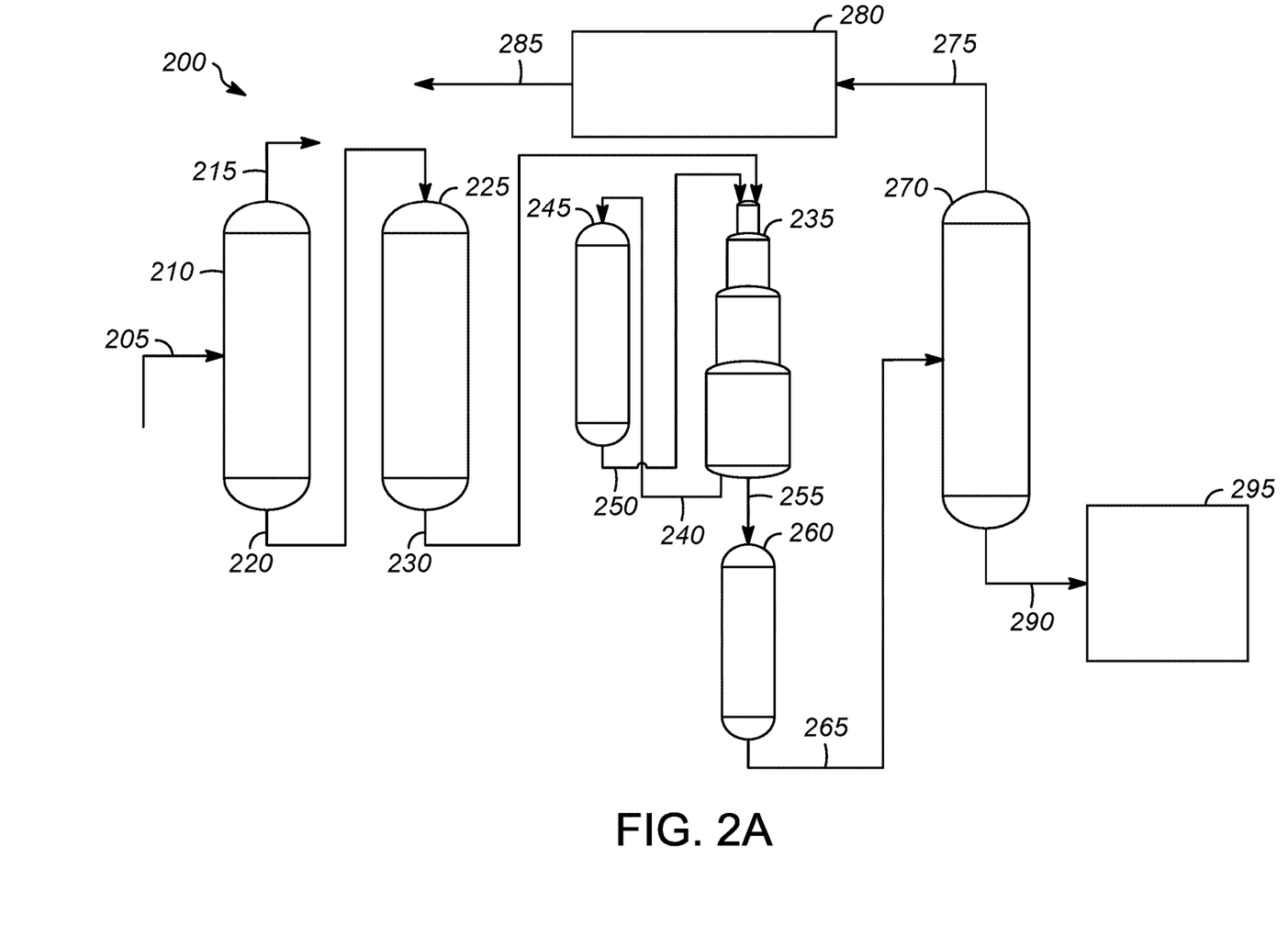
FIG. 2A is an illustration of one embodiment of a process for converting naphtha into aromatics according to the present invention.

FIG. 2A shows one embodiment of a process 200 for converting naphtha into aromatics. The naphtha feed 205 is sent to a naphtha splitter 210 where it is separated into an overhead stream 215 having a T5 boiling point in a range of about 0° C. to about 34° C. and a T95 boiling point in a range of about 20° C. to about 82° C. and a bottoms stream 220 having a T5 boiling point in a range of about 20° C. to about 82° C. and a T95 boiling point in a range of about −140° C. to about 215° C. The bottoms stream 220 is sent to a naphtha hydrotreating zone 225. The naphtha hydrotreating zone 225 may be used to prepare the bottoms stream 220 for downstream reforming with sensitive noble metal catalyst systems. In an exemplary process, the bottoms stream 220 is brought into the naphtha hydrotreating zone 225, mixed with hydrogen, and heated to a reaction temperature over a hydrotreating catalyst. Exemplary hydrotreating catalysts include metals from CAS Group VIB, VIIB, VIII, and combinations thereof. The naphtha hydrotreating zone 225 may have multiple distinct stages with different catalytic zones. For example, the first stage can be operated at low temperature (e.g., about 40° C. to about 250° C.) for mainly diolefin removal, and the second stage can be operated at higher temperature (e.g., up to about 400° C.) for olefin, sulfur, and nitrogen content reduction. For a single stage, exemplary reaction temperatures are from about 250° C. to about 400° C. The main catalytic reactions in naphtha hydrotreating zone 225 convert the contaminants of noble metal catalyst systems, such as sulfur, nitrogen, and oxygenates, via hydrogenolysis reactions to hydrogen sulfide, ammonia, and water so that they can be removed from the naphtha stream. Metals in the naphtha may be removed by adsorption onto the catalyst. As a result, olefins and/or diolefins are also saturated.

The resulting hydrotreated stream 230 contains paraffins, naphthenes and aromatics, and low levels of olefins and is fed to a reforming zone for conversion of paraffins and naphthenes into aromatics. An exemplary reforming zone is a catalytic reformer 235 with a continuous catalyst regeneration (CCR) unit 245. The reformer 235 may be operated at a temperature of from about 450° C. to about 560° C. A catalyst stream 240 from the bottom of the reformer 235 is sent to a catalyst regenerator 245. The regenerated catalyst 250 is sent to the top of the reformer 235. Alternative the catalyst in the reforming zone can be regenerated in cyclic fashion by taking one of multiple reactors off-line for in situ regeneration in cyclical fashion or in semi-regenerative mode where all reactors are taken offline for in situ regeneration at one time.

Compounds in the hydrotreated stream 230 are reformed to produce a reformer effluent stream 255. Specifically, naphthenes are dehydrogenated to form aromatics, normal paraffins are isomerized to form isoparaffins, and paraffins are dehydrocyclized, i.e., dehydrogenated and aromatized, to form aromatics.

The reformer effluent 255 is heated and sent directly to an acid cracking reaction zone 260 without separating the reformer effluent 255 into different streams with different compositions. The reformer effluent 255 is reacted to form cracked olefins comprising at least one of ethylene, propylene, and butylenes.

The cracked reformer effluent 265 comprising the aromatics and the olefins is sent to a stripper column 270 (for example a depentanizer or debutanizer column) where an overhead stream 275 is removed. The overhead stream 275 is sent to a steam cracker 280 where it is cracked to form additional olefins comprising at least one of ethylene, propylene, and/or butylene. Stream 285 comprises the cracked olefins from the acid cracking reaction zone 260 and the additional olefins formed in the steam cracker 280, and heavier components.

The aromatics stream 290 from the stripper column 270 is sent to the aromatics complex 295 for separation.

Figure 2B:
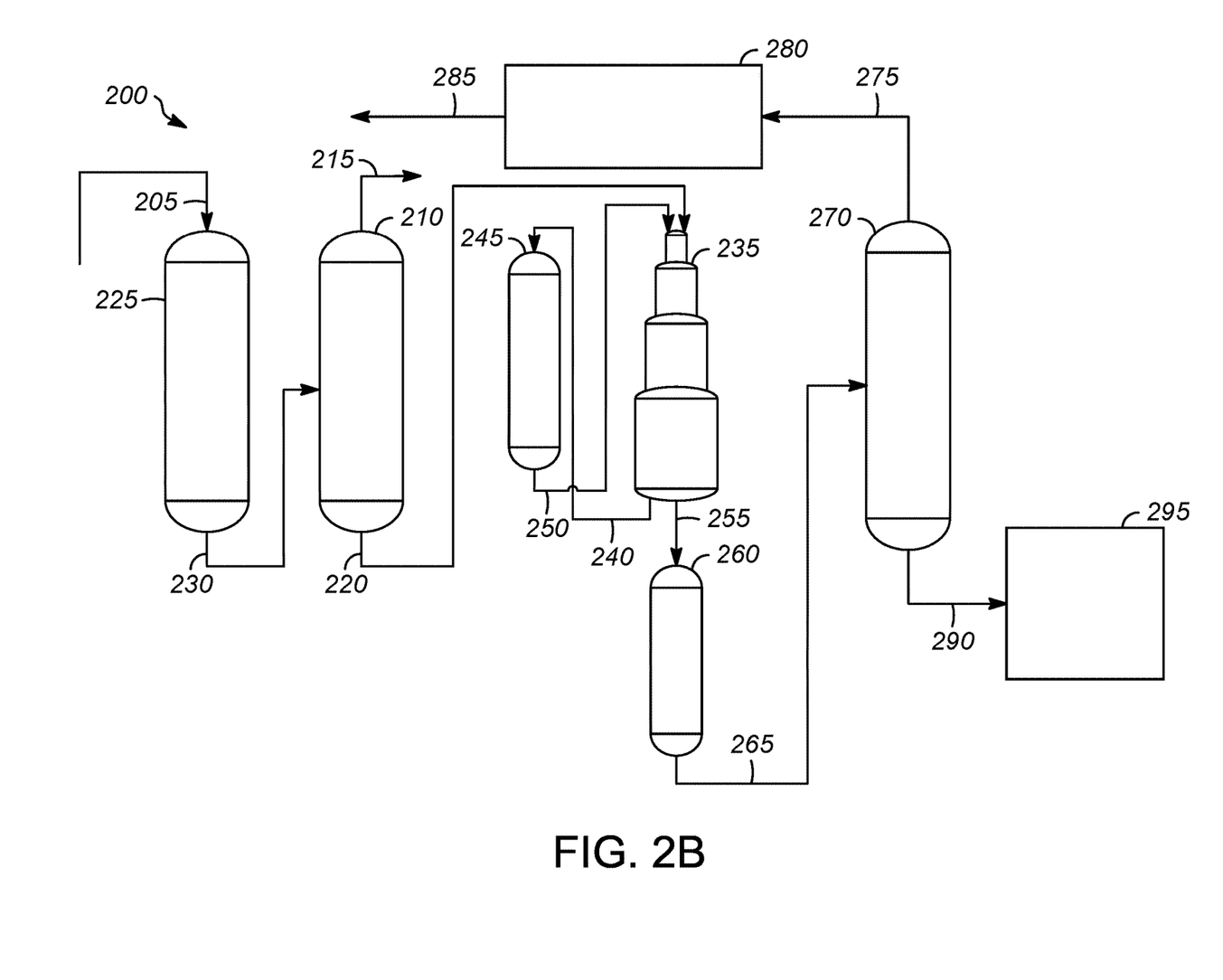
FIG. 2B is another embodiment of a process for converting naphtha into aromatics according to the present invention.

FIG. 2B is similar to FIG. 2A, except that the naphtha feed stream is sent to the naphtha hydrotreater before it goes to the naphtha splitter to provide a hydrotreated overhead stream. The naphtha feed 205 is sent to a naphtha hydrotreating zone 225, The hydrotreated naphtha stream 230 is sent to a naphtha splitter 210 where it is separated into a hydrotreated overhead stream 215 having a T5 boiling point in a range of about 0° C. to about 34° C. and a T95 boiling point in a range of about 20° C. to about 82° C. and a hydrotreated bottoms stream 220 having a T5 boiling point in a range of about 20° C. to about 82° C. and a T95 boiling point in a range of about 140° C. to about 215° C. The hydrotreated bottoms stream 220 is sent to the reformer 235.

Figure 3:
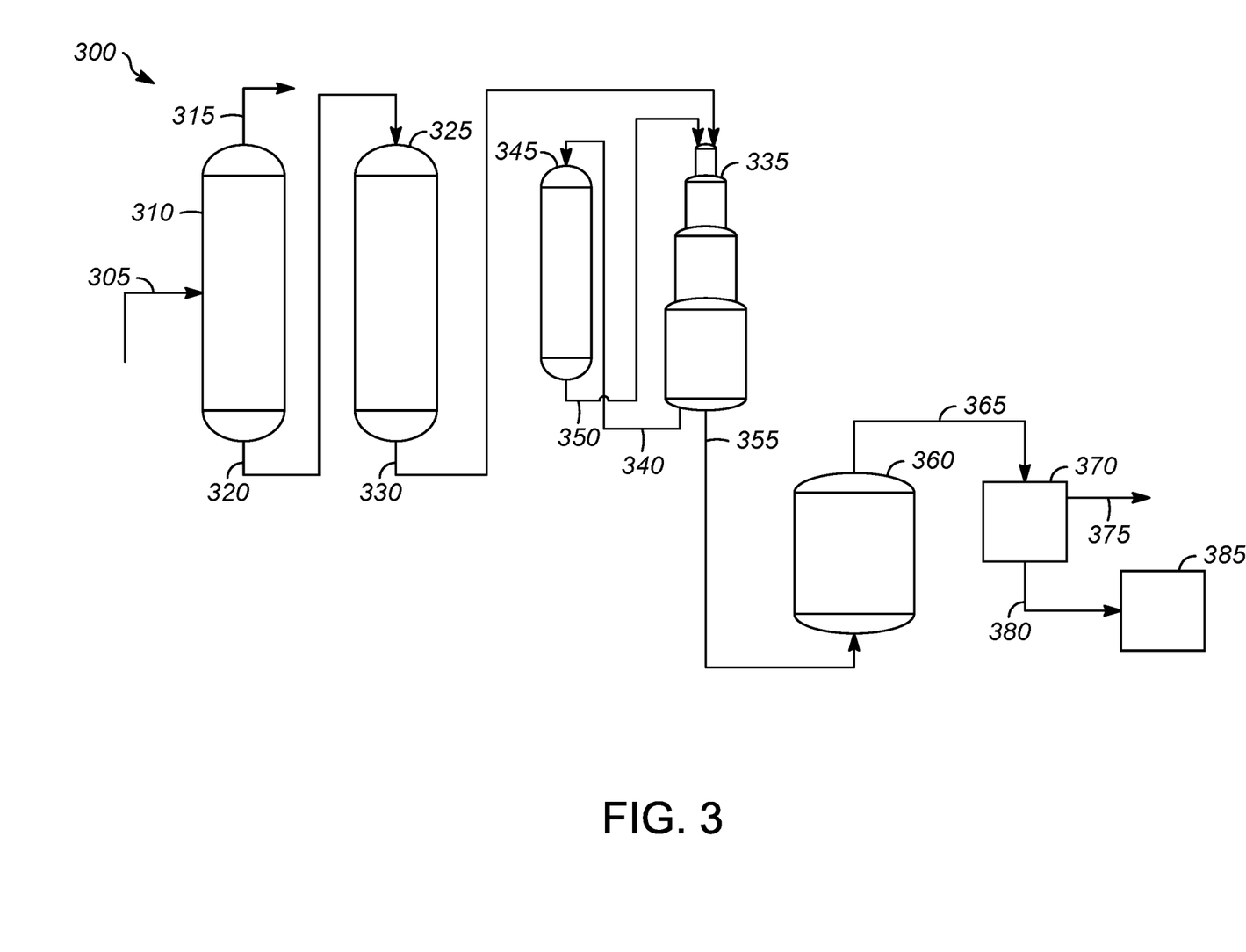
FIG. 3 is another embodiment of a process for converting naphtha into aromatics according to the present invention.

FIG. 3 illustrates another embodiment of the process 300 for converting naphtha into aromatics. The naphtha feed 305 is sent to a naphtha splitter 310 where it is separated into an overhead stream 315 having a T5 boiling point in a range of about 0° C. to about 34° C. and a T95 boiling point in a range of about 20° C. to about 82° C. and a bottoms stream 320 having a T5 boiling point in a range of about 20° C. to about 82° C. and a T95 boiling point in a range of about −140° C. to about 215° C. The bottoms stream 320 is sent to a naphtha hydrotreating unit 325 for hydrotreating as discussed above. Alternatively the naphtha splitter can be after the naphtha hydrotreater if it is desired to have a hydrotreated overhead stream.

The hydrotreated stream 330 which contains paraffins, naphthenes and aromatics and low levels of olefins, is fed to a reforming zone for conversion into aromatics. The reforming zone can be a catalytic reformer 335 with a CCR unit 345, as discussed above. The catalyst can be regenerated by sending a catalyst stream 340 from the bottom of the reformer 335 to the CCR unit 345. The regenerated catalyst 350 is sent to the top of the reformer 335.

Compounds in the hydrotreated stream 330 are reformed to produce a reformer effluent stream 355. As discussed above, naphthenes are dehydrogenated to form aromatics, normal paraffins are isomerized to form isoparaffins, and paraffins are dehydrocyclized, i.e., dehydrogenated and aromatized, to form aromatics.

The reformer effluent 355 is heated and sent directly to a silicalite cracking reaction zone 360 without separating the reformer effluent 355 into streams with different compositions. In this embodiment, the cracking catalyst comprises ZSM-5, such as silicalite. The silicalite typically has a molar ratio of zeolite silica to alumina of greater than about 250, or greater than about 300, or greater than about 400, or greater than about 500.

The silicalite cracking reaction zone 360 is operated at a temperature in the range of about 450° C. to about 700° C., or about 485° C. to about 650° C., and a pressure of about 30 kPa (g) (4 psig) to about 1034 kPa (g) (150 psig), or about 30 kPa (g) (4 psig) to about 750 kPa (g) (109 psig). The molar ratio of hydrogen to hydrocarbon is typically in the range of about 0.5:1 to about 10:1, and the weight hourly space velocity (WHSV) of about 0.1 $hr^{-1}$ to about 10 $hr^{-1}$. The reformer effluent 355 is reacted to form cracked olefins comprising at least one of ethylene, propylene, and butylene.

The cracked reformer effluent 365 comprising the aromatics and the olefins is sent to a separation zone 370 where a light olefin stream 375 is removed and can be further purified to petrochemical components comprising at least one of ethylene, propylene and butylene. The aromatic stream 380 is sent to the aromatics complex 385 for further processing.

As will be understood by those of skill in the art, the figures do not show all of the equipment involved in these processes. There may be heat exchanger, coolers, flash drums, other component separators such as membranes or adsorbent, compressors, or pumps and the like between the various pieces of equipment that are shown.

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a process for making aromatics comprising reforming a naphtha stream in a reforming zone under reforming conditions to form a reformer effluent comprising aromatic compounds and non-aromatic compounds, wherein at least a portion of the aromatic compounds contain alkyl groups; heating the reformer effluent and passing the reformer effluent directly to an acid cracking reaction zone; selectively cracking the non-aromatic compounds and selectively dealkylating at least a portion of the alkyl groups on the aromatic compounds in the presence of an acid cracking catalyst in the acid cracking reaction zone under acid cracking conditions to form a cracked reformer effluent comprising the aromatic compounds and cracked olefins. An embodiment of the invention is one, any or all of prior embodiments in this paragraph up through the first embodiment in this paragraph wherein the cracked olefins comprise at least one of ethylene, propylene, and butylene, and further comprising recovering the cracked olefins, wherein the recovered cracked olefins are greater than about 95 wt % pure. An embodiment of the invention is one, any or all of prior embodiments in this paragraph up through the first embodiment in this paragraph wherein the acid cracking catalyst comprises ZSM-5. An embodiment of the invention is one, any or all of prior embodiments in this paragraph up through the first embodiment in this paragraph wherein the acid cracking catalyst comprises a silicalite catalyst having a zeolite silica to alumina molar ratio of greater than about 250. An embodiment of the invention is one, any or all of prior embodiments in this paragraph up through the first embodiment in this paragraph further comprising separating the cracked reformer effluent into an aromatic lean fraction comprising the cracked olefins and an aromatic rich fraction comprising the aromatic compounds; and recovering the aromatic rich fraction. An embodiment of the invention is one, any or all of prior embodiments in this paragraph up through the first embodiment in this paragraph further comprising passing at least about 75 wt % of the recovered aromatic rich fraction directly to an aromatics complex. An embodiment of the invention is one, any or all of prior embodiments in this paragraph up through the first embodiment in this paragraph further comprising steam cracking the aromatic lean fraction in a steam cracking reaction zone to form additional olefins, the additional olefins comprising at least one of ethylene, propylene, and butylene; and recovering the additional olefins. An embodiment of the invention is one, any or all of prior embodiments in this paragraph up through the first embodiment in this paragraph wherein the acid cracking conditions include at least one of a temperature in the range of about 450° C. to about 700° C., a pressure in a range of about 30 kPa (g) to about 1034 kPa (g), a hydrogen to hydrocarbon ratio of at least about 0.51 to about 101, and a weight hourly space velocity (WHSV) of about 0.1 hr-1 to about 10 hr-1. An embodiment of the invention is one, any or all of prior embodiments in this paragraph up through the first embodiment in this paragraph wherein the acid cracking reaction zone comprises a fixed bed reactor, an ebullated bed reactor, or a continuous catalyst regenerator. An embodiment of the invention is one, any or all of prior embodiments in this paragraph up through the first embodiment in this paragraph further comprising introducing a naphtha feed stream into a naphtha splitter column to form at least two streams, the first stream having a T5 boiling point in a range of about 0° C. to about 34° C. and a T95 boiling point in a range of about 25° C. to about 82° C. and the second stream having a T5 boiling point in a range of about 20° C. to about 82° C. and a T95 boiling point in a range of about 140° C. to about 215° C.; passing the second stream to a naphtha hydrotreating reaction zone forming a hydrotreated naphtha stream; and wherein reforming the naphtha stream comprises reforming the hydrotreated naphtha stream. An embodiment of the invention is one, any or all of prior embodiments in this paragraph up through the first embodiment in this paragraph further comprising passing at least a portion of the first stream to the acid cracking reaction zone and selectively cracking the hydrocarbons in the first stream. An embodiment of the invention is one, any or all of prior embodiments in this paragraph up through the first embodiment in this paragraph further comprising introducing a naphtha feed stream into a naphtha hydrotreating reaction zone forming a hydrotreated naphtha stream; passing the hydrotreated naphtha stream to a naphtha splitter column to form at least two streams, the first hydrotreated stream having a T5 boiling point in a range of about 0° C. to about 34° C. and a T95 boiling point in a range of about 25° C. to about 82° C. and the second hydrotreated stream having a T5 boiling point in a range of about 20° C. to about 82° C. and a T95 boiling point in a range of about 140° C. to about 215° C.; and wherein reforming the naphtha stream comprises reforming the second hydrotreated stream. An embodiment of the invention is one, any or all of prior embodiments in this paragraph up through the first embodiment in this paragraph further comprising introducing an additional stream comprising hydrocarbons to the acid cracking reaction zone and selectively cracking the hydrocarbons in the additional stream.

A second embodiment of the invention is a process for making aromatics, and at least one of ethylene, propylene, and butylene comprising reforming a naphtha stream in a reforming zone under reforming conditions to form a reformer effluent comprising aromatic compounds and non-aromatic compounds, wherein at least a portion of the aromatic compounds contain alkyl groups; heating the reformer effluent and passing the reformer effluent directly to an acid cracking reaction zone; selectively cracking the non-aromatic compounds and selectively dealkylating at least a portion of the alkyl groups on the aromatic compounds in the presence of an acid cracking catalyst in the acid cracking reaction zone under acid cracking conditions to form a cracked reformer effluent comprising the aromatic compounds and cracked olefins, wherein the cracked olefins comprise at least one of ethylene, propylene, and butylene; separating the cracked reformer effluent into an aromatic lean fraction comprising the cracked olefins and an aromatic rich fraction comprising the aromatic compounds; and passing the aromatic rich fraction to an aromatics complex. An embodiment of the invention is one, any or all of prior embodiments in this paragraph up through the second embodiment in this paragraph wherein the acid cracking conditions include at least one of a temperature in the range of about 4550° C. to about 700° C., a pressure in a range of about 30 kPa (g) to about 1034 kPa (g), a hydrogen to hydrocarbon ratio of at least about 0.51 to about 101, and a weight hourly space velocity (WHSV) of about 0.1 hr-1 to about 10 hr-1. An embodiment of the invention is one, any or all of prior embodiments in this paragraph up through the second embodiment in this paragraph further comprising introducing a naphtha feed stream into a naphtha splitter column to form at least two streams, the first stream having a T5 boiling point in a range of about 0° C. to about 34° C. and a T95 boiling point in a range of about 20° C. to about 82° C. and the second stream having a T5 boiling point in a range of about 20° C. to about 82° C. and a T95 boiling point in a range of about −140° C. to about 215° C.; passing the second stream to a naphtha hydrotreating reaction zone forming a hydrotreated naphtha stream; and wherein reforming the naphtha stream comprises reforming the hydrotreated naphtha stream. An embodiment of the invention is one, any or all of prior embodiments in this paragraph up through the second embodiment in this paragraph further comprising introducing a naphtha feed stream into a naphtha hydrotreating reaction zone forming a hydrotreated naphtha stream; passing the hydrotreated naphtha stream to a naphtha splitter column to form at least two streams, the first hydrotreated stream having a T5 boiling point in a range of about 0° C. to about 34° C. and a T95 boiling point in a range of about 25° C. to about 82° C. and the second hydrotreated stream having a T5 boiling point in a range of about 20° C. to about 82° C. and a T95 boiling point in a range of about 140° C. to about 215° C.; and wherein reforming the naphtha stream comprises reforming the second hydrotreated stream.

A third embodiment of the invention is an apparatus comprising a reforming zone having an inlet and an outlet; an acid cracking reaction zone having an inlet and an outlet, the inlet of the acid cracking zone being in fluid communication with the outlet of the reforming zone; a fractionation column having an inlet, an overhead outlet, and a bottoms outlet, the inlet of the fractionation zone being in fluid communication with the outlet of the acid cracking reaction zone; and an aromatics recovery zone having an inlet and an outlet, the inlet of the aromatic recovery zone being in fluid communication with the bottoms outlet of the fractionation zone. An embodiment of the invention is one, any or all of prior embodiments in this paragraph up through the third embodiment in this paragraph further comprising a naphtha splitter column having an inlet, an overhead outlet and a bottoms outlet, a naphtha hydrotreating reaction zone having an inlet and an outlet, the inlet of the naphtha hydrotreating reaction zone being in fluid communication with the bottoms outlet of the naphtha splitter column, and the outlet of the naphtha hydrotreating reaction zone being in fluid communication with the inlet of the reforming zone. An embodiment of the invention is one, any or all of prior embodiments in this paragraph up through the third embodiment in this paragraph further comprising a steam cracking reaction and recovery zone having an inlet and an outlet, the inlet of the stream cracking reaction and recovery zone being in fluid communication with the overhead outlet of the fractionation column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for making aromatics comprising:
reforming a naphtha stream in a reforming zone under reforming conditions to form a reformer effluent comprising aromatic compounds and non-aromatic compounds, wherein at least a portion of the aromatic compounds contain alkyl groups;
heating the reformer effluent and passing the reformer effluent directly to an acid cracking reaction zone;
selectively cracking the non-aromatic compounds and selectively dealkylating at least a portion of the alkyl groups on the aromatic compounds in the presence of an acid cracking catalyst in the acid cracking reaction zone under acid cracking conditions to form a cracked reformer effluent comprising the aromatic compounds and cracked olefins, and wherein the acid cracking catalyst consists of a silicalite catalyst having a silica to alumina molar ratio of greater than about 250, the acid cracking catalyst being without a hydrogenating metal function.

2. The process of claim 1 wherein the cracked olefins comprise at least one of ethylene, propylene, and butylene, and further comprising:
recovering the cracked olefins, wherein the recovered cracked olefins are greater than about 95 wt % pure.

3. The process of claim 1 further comprising:
separating the cracked reformer effluent into an aromatic lean fraction comprising the cracked olefins and an aromatic rich fraction comprising the aromatic compounds; and
recovering the aromatic rich fraction.

4. The process of claim 3 further comprising:
passing at least about 75 wt % of the recovered aromatic rich fraction directly to an aromatics complex.

5. The process of claim 3 further comprising:
steam cracking the aromatic lean fraction in a steam cracking reaction zone to form additional olefins, the additional olefins comprising at least one of ethylene, propylene, and butylene; and
recovering the additional olefins.

6. The process of claim 1 wherein the acid cracking conditions include at least one of a temperature in the range of about 450° C. to about 700° C., a pressure in a range of about 30 kPa (g) to about 1034 kPa (g), a hydrogen to hydrocarbon ratio of at least about 0.5:1 to about 10:1, and a weight hourly space velocity (WHSV) of about 0.1 hr$^{-1}$ to about 10 hr$^{-1}$.

7. The process of claim 1 wherein the acid cracking reaction zone comprises a fixed bed reactor, an ebullated bed reactor, or a continuous catalyst regenerator.

8. The process of claim 1 further comprising:
introducing a naphtha feed stream into a naphtha splitter column to form at least two streams, the first stream having a T5 boiling point in a range of about 0° C. to about 34° C. and a T95 boiling point in a range of about 25° C. to about 82° C. and the second stream having a T5 boiling point in a range of about 20° C. to about 82° C. and a T95 boiling point in a range of about 140° C. to about 215° C.;
passing the second stream to a naphtha hydrotreating reaction zone forming a hydrotreated naphtha stream; and
wherein reforming the naphtha stream comprises reforming the hydrotreated naphtha stream.

9. The process of claim 8 further comprising:
passing at least a portion of the first stream to the acid cracking reaction zone and selectively cracking the hydrocarbons in the first stream.

10. The process of claim 1 further comprising:
introducing a naphtha feed stream into a naphtha hydrotreating reaction zone forming a hydrotreated naphtha stream;
passing the hydrotreated naphtha stream to a naphtha splitter column to form at least two streams, the first hydrotreated stream having a T5 boiling point in a range of about 0° C. to about 34° C. and a T95 boiling point in a range of about 25° C. to about 82° C. and the second hydrotreated stream having a T5 boiling point in a range of about 20° C. to about 82° C. and a T95 boiling point in a range of about 140° C. to about 215° C.; and
wherein reforming the naphtha stream comprises reforming the second hydrotreated stream.

11. The process of claim 1 further comprising:
introducing an additional stream comprising hydrocarbons to the acid cracking reaction zone and selectively cracking the hydrocarbons in the additional stream.

12. A process for making aromatics, and at least one of ethylene, propylene, and butylene comprising:
reforming a naphtha stream in a reforming zone under reforming conditions to form a reformer effluent comprising aromatic compounds and non-aromatic compounds, wherein at least a portion of the aromatic compounds contain alkyl groups;
heating the reformer effluent and passing the reformer effluent directly to an acid cracking reaction zone;
selectively cracking the non-aromatic compounds and selectively dealkylating at least a portion of the alkyl groups on the aromatic compounds in the presence of an acid cracking catalyst in the acid cracking reaction zone under acid cracking conditions to form a cracked reformer effluent comprising the aromatic compounds and cracked olefins, wherein the cracked olefins comprise at least one of ethylene, propylene, and butylene, and wherein the acid cracking catalyst consists of a silicalite catalyst having a silica to alumina molar ratio of greater than about 250, the acid cracking catalyst being without a hydrogenating metal function;
separating the cracked reformer effluent into an aromatic lean fraction comprising the cracked olefins and an aromatic rich fraction comprising the aromatic compounds; and
passing the aromatic rich fraction to an aromatics complex.

13. The process of claim 12 wherein the acid cracking conditions include at least one of a temperature in the range of about 450° C. to about 700° C., a pressure in a range of about 30 kPa (g) to about 1034 kPa (g), a hydrogen to hydrocarbon ratio of at least about 0.5:1 to about 10:1, and a weight hourly space velocity (WHSV) of about 0.1 hr$^{-1}$ to about 10 hr$^{-1}$.

14. The process of claim 12 further comprising:
introducing a naphtha feed stream into a naphtha splitter column to form at least two streams, the first stream having a T5 boiling point in a range of about 0° C. to about 34° C. and a T95 boiling point in a range of about 20° C. to about 82° C. and the second stream having a T5 boiling point in a range of about 20° C. to about 82° C. and a T95 boiling point in a range of about 140° C. to about 215° C.;
passing the second stream to a naphtha hydrotreating reaction zone forming a hydrotreated naphtha stream; and
wherein reforming the naphtha stream comprises reforming the hydrotreated naphtha stream.

15. The process of claim 12 further comprising:
introducing a naphtha feed stream into a naphtha hydrotreating reaction zone forming a hydrotreated naphtha stream;
passing the hydrotreated naphtha stream to a naphtha splitter column to form at least two streams, the first hydrotreated stream having a T5 boiling point in a range of about 0° C. to about 34° C. and a T95 boiling point in a range of about 25° C. to about 82° C. and the second hydrotreated stream having a T5 boiling point in a range of about 20° C. to about 82° C. and a T95 boiling point in a range of about 140° C. to about 215° C.; and
wherein reforming the naphtha stream comprises reforming the second hydrotreated stream.

* * * * *